(12) United States Patent
Long et al.

(10) Patent No.: US 8,007,742 B2
(45) Date of Patent: Aug. 30, 2011

(54) IRIS DIGESTER-EVAPORATOR INTERFACE

(75) Inventors: Stephen E. Long, Gaithersburg, MD (US); David M. Bunk, Bethesda, MD (US); Mariana Arce-Osuna, Queretaro (ME)

(73) Assignee: United States of America as represented by the Secretary of Commerce, Washington, DC (US)

( * ) Notice: Subject to any disclaimer, the term of this patent is extended or adjusted under 35 U.S.C. 154(b) by 1467 days.

(21) Appl. No.: 11/438,390

(22) Filed: May 23, 2006

(65) Prior Publication Data

US 2007/0272850 A1    Nov. 29, 2007

Related U.S. Application Data

(60) Provisional application No. 60/718,453, filed on Sep. 20, 2005.

(51) Int. Cl.
*G01N 30/72* (2006.01)
(52) U.S. Cl. .......... 422/530; 422/70; 422/528; 422/547; 436/161; 436/173; 436/175; 436/177
(58) Field of Classification Search .................... 422/99, 422/101, 102, 70, 528, 530, 547; 436/161, 436/173, 175, 177; 73/61.58
See application file for complete search history.

(56) References Cited

U.S. PATENT DOCUMENTS

| | | | |
|---|---|---|---|
| 4,290,893 A | 9/1981 | Hare et al. | |
| 5,205,154 A | 4/1993 | Lee et al. | |
| 5,559,036 A * | 9/1996 | Mienie et al. | 436/63 |
| 6,166,379 A | 12/2000 | Montaser et al. | |
| 2002/0050470 A1 | 5/2002 | Jinno et al. | |
| 2004/0020834 A1 | 2/2004 | Mincsovics et al. | |
| 2004/0138445 A1 | 7/2004 | Thorre | |
| 2005/0163723 A1 | 7/2005 | Foster et al. | |
| 2005/0230617 A1 | 10/2005 | Montaser et al. | |

OTHER PUBLICATIONS

"Analytical Method Development for Selenium-Containing Proteins of Clinical Interest"—A Dissertation presented by Mariana Arce-Osuna, Sep. 2005.

* cited by examiner

*Primary Examiner* — Jan M Ludlow
(74) *Attorney, Agent, or Firm* — Novak Druce + Quigg LLP

(57) ABSTRACT

A digester-evaporator for partially digesting a sample and for evaporating the solvent after partial digestion. The digester includes at least one reaction coil; a heating element arranged along a portion of the reaction coil; at least a portion of the reaction coil proximate to its output being preheated by the heating element to a degree sufficient to convert a partially digested sample into vapor; a collector spoon with carrier water for collecting sample vapor; and an evaporator portion including an evaporation chamber including a substantially vertically-oriented tube The collector spoon is arranged in the top of the substantially vertically-oriented tube, and a gas supply tube for supplying a preheated gas provided in a top of the substantially vertically-oriented tube so as to create a cyclonic gas flow into the chamber and carry the sample to a container area in a bottom portion of the chamber.

11 Claims, 6 Drawing Sheets

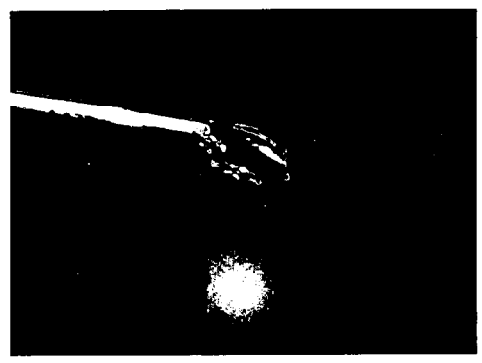
FIG. 5A
FIG. 5B
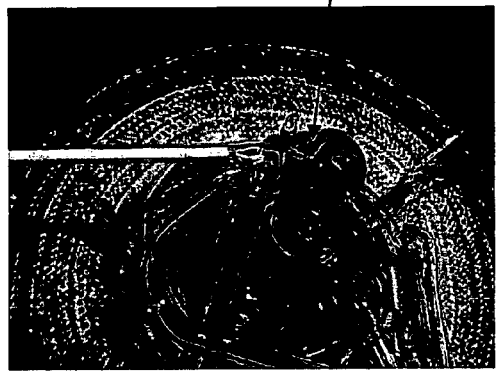
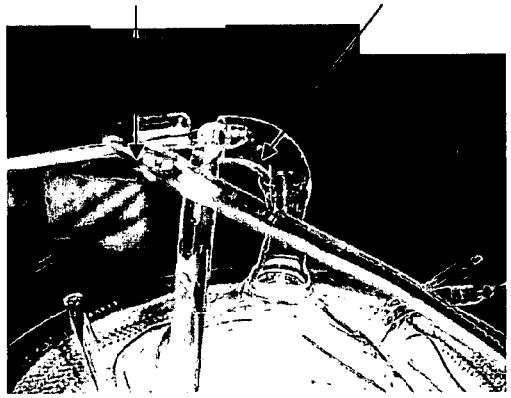
FIG. 6A
FIG. 6B

IRIS DIGESTER-EVAPORATOR INTERFACE

This application claims priority from U.S. provisional application Ser. 60/718,453 filed Sep. 20, 2005.

BACKGROUND OF THE INVENTION

1. Field of the Invention

The present device relates to analytic methods and devices for separation and quantification. More particularly, the present invention relates to the separation and quantification of selenium containing proteins and devices that support the process of separation and quantification.

2. Description of the Related Art

There are a number of essential micronutrients in both humans and animals, and many cases their significance is not fully understood. For example, selenium (Se), which is found in both humans and animals in almost trace amounts, can be used as an accurate health marker. Lower than normal levels of Se in humans can affect reproduction, immuno-response, miscarriage rate and thyroid function (to name just a few areas), as well as suppression of the destruction of free radicals that may be responsible for the formation of certain types of cancer. Typically, elements such as Se are found within a human or animal body in proteins, which in this case are referred to as, for example, selenoamino acids (selenocysteine and selenomethionine).

There are several studies that support the finding that the measurement of selenium-containing proteins are better health markers than a "total" selenium count. In fact, the main selenium-containing proteins found in human serum and plasma are albumin, gluthathione peroxidase (GSHPx) and selenoprotein P (SepP), see Arce-Osuna, M., *DISSERTATION: ANALYTICAL METHOD DEVELOPMENT FOR SELENIUN-CONTAINING PROTEINS OF CLINICAL INTEREST*, University of Massachusetts, Analytical Chemistry Department, Amherst Ma, September 2005, incorporated herein by reference.

The most common techniques used for the separation, identification and quantification of selenium containing proteins are mainly based on antibody specificity and affinity chromatographic processes. For example, to separate the selenium-containing protein, techniques such as immunoassay, anion exchange chromatography, heparin affinity chromatography, immobilized metal affinity chromatography (IMAC) and size exclusion (SEC) have been used in the art with some degree of success.

In addition, protein identification has been accomplished by a combination of chromatographic retention time, sodium dodecylsulphate polyacrylamide gel electrophoresis (SDS-PAGE) analysis, and GSHPx activity of chromatographic fractions.

Quantification of the amount of selenium (as well as sulfur) in a sample has been performed by using inductively coupled plasma mass spectrometry (ICP-MS), atomic absorption spectrometry (AAS), and by derivatization for fluorimetric detection. However, some of the major disadvantages of the aforementioned methods include poor reproducibility, specificity, inadequate sensitivity, analyte losses, and contamination.

In order to determine the amount of selenium in each protein, there are salts contained within the mobile phases (buffers) for affinity chromatography, and organic solvents used in reversed phased chromatography pose a problem when a coupled liquid chromatograph inductively coupled plasma mass spectrometry (LC-ICP-MS) instrument is used. More specifically, the high concentration of salts (above 0.5 to 1.0 g/mL$^{-1}$) in ICP-MS, in most cases, has a detrimental effect on the analyte signal because of matrix effects. In addition, the organic solvent that is typically used in chromatography is also a problem in ICP-MS measurements. There is a problem in that the high vapor pressure in the spray chamber reduces the analyte transport to the plasma torch, and at high concentrations, reduces the effective ionization power of the plasma. The results is a significant ICP-MS background drift resulting from a chromatographic gradient run. Sending organic solvents into an ICP-MS may also cause the build-up of carbon in the sampling cones. FIG. 1 is a photo showing some of the carbon build-up that can occur.

Moreover, the problems encountered when an inductively coupled plasma mass spectrometry (ICP-MS) unit was coupled directly to the continuous flow from reversed phase liquid chromatograph includes a high background signal, first increasing and then decreasing in magnitude during the course of a chromatographic gradient solvent, as well as the aforementioned carbon build-up and transport difficulties.

There have been attempts to reduce the concentration of the organic solvent that reaches the ICP-MS and/or reduce the amount of effluent that arrives at the ICP-MS. It is, for example, a common practice to add a small amount of oxygen to a nebuliser gas flow and to operate the plasma at high power in order to make the system more robust to the effects of organic solvent.

For example, desolvated aerosol has been produced in a number of different ways, such as combining thermospray or ultrasonic nebulisers with a membrane desolvator, or connecting a membrane with cryogenic cooling. However, these approaches still result in a low concentration of organic solvent being introduced into the ICP. Therefore, it is still very difficult to eliminate residual solvent from an ICP spray chamber after each chromatographic run, such that a subsequent chromatographic run is affected by the previous run, having an affect on the integrity of the measurements.

Accordingly, research conclusions might be affected by the uncertainty or the bias of the methods used, and there is a need in the art for a more accurate quantification of both selenium and selenium-containing protein.

SUMMARY OF THE INVENTION

The inventors have created an IRIS Digester-Evaporator (IRIS-DE) interface device that overcomes the problems encountered when an inductively coupled plasma mass spectrometry (ICP-MS) unit is coupled directly to the continuous flow from a reversed phase liquid high performance chromatography (RC-HPLC). The present invention provides an apparatus and a method for interfacing the IRIS-DE to couple an RP-HPLC with an ICP-MS system so as to be able to quantify certain micronutrients with an accuracy and reliability heretofore unknown.

The IRIS-DE interface device, can, for example, be used to process the HPLC effluent by digesting the sample with nitric acid, evaporating the undesirable high concentration excess of nitric acid and solvent in-line, and sending the sample to the ICP-MS in a high aqueous solvent stream. The present invention serves to eliminate all of the organic solvent n-line and the conditions (nitrogen flow, carrier water, temperature) can be optimized for each application. The dimensions can be modified to suit different flow rates.

Additionally, the system is able to partially digest the analyte before the solvent evaporation process. These processes improve analyte transport to the ICP, permitting efficient analyte excitation and ionization, and drastically reduce the carbon that tends to build up on the ICP-MS cones after extended use. The IRIS-DE can be cleaned online, by stopping the nitrogen flow, carrier water, and HPLC effluent flow, raising the temperature and then flushing the water.

An IRIS-DE interface digestion apparatus according to the present invention includes a high pressure polyetherketone (PEEK) tee that receives the flow from an HPLC system, mixes the flow with nitric acid, and then passes the mixture to a PEEK reaction coil to premix and start the acid digestion process. The PEEK reaction coil is connected to a second preheated reaction coil made of quartz wherein the sample is partially digested and transferred to the vapor phase.

BRIEF DESCRIPTION OF THE DRAWINGS

For purposes of illustration and not intended to limit the scope of the invention in any way, the aforementioned and other characteristics of the invention will be clear from the following description of a preferred form of the embodiments, given as non-restrictive examples, with reference to the attached drawings wherein:

FIGS. 5A and 5B are photographs of an actual collector spoon that can be used with and IRIS-DE according to the present invention;

FIGS. 6A and 6B are photos showing the alignment between the quartz coil, collector spoon, the nitrogen gas flow line, and the top entrance of the evaporator;

DETAILED DESCRIPTION OF THE INVENTION

It is understood by a person of ordinary skill in the art that the drawings are presented for purposes of illustration and not for limitation. The embodiments shown and described herein do not encompass all possible variations of the arrangement of structure or the type of substances that can be quantified thereby. Therefore, an artisan appreciates that many modifications can be made within the spirit of the invention and the scope of the appended claims than the illustrative examples shown and described.

Figure 1:
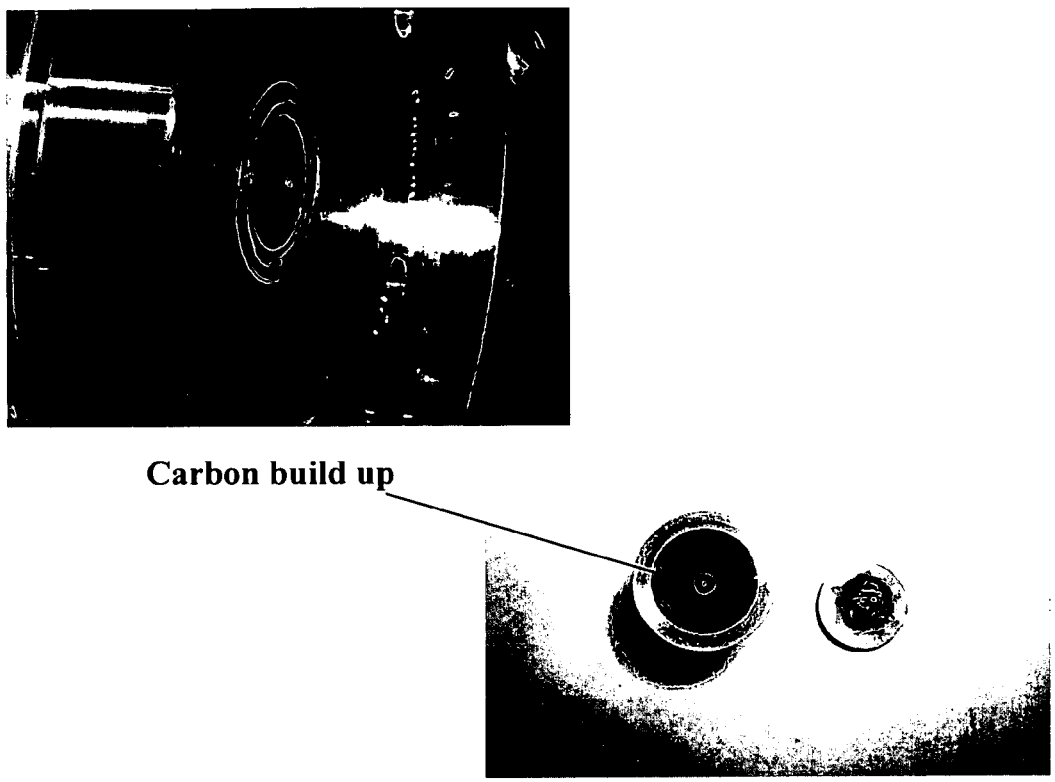
FIG. 1 is a photo showing the carbon build-up that occurs with the prior art processes of quantification.
Figure 2:
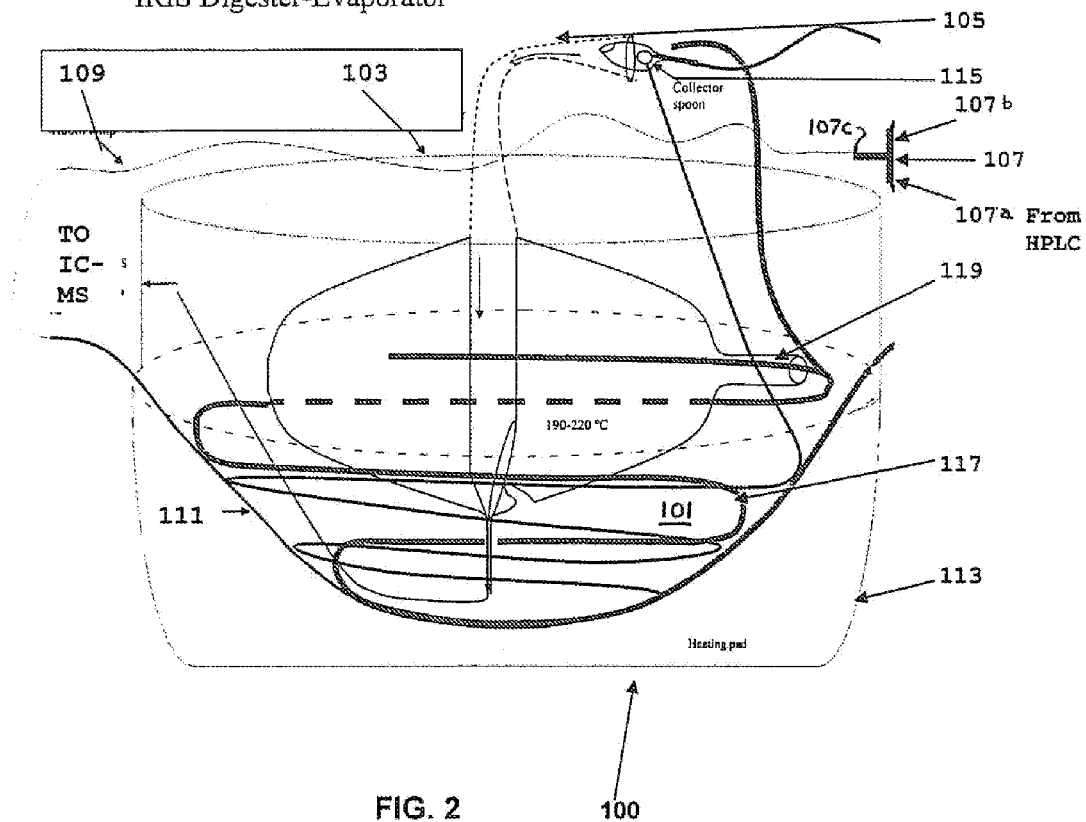
FIG. 2 is a schematic of an IRIS Digester-Evaporator (IRIS-DE) interface device according to the present invention.

FIG. 2 is a front view of IRIS-DE interface device. The IRIS-DE 100 has a chamber 101, which is typically constructed of a glass housing. There is both a digester portion and a evaporator portion. Within the device 100, there exists a temperature gradient, with a higher temperature in the digester portion than in the evaporator. A top cover 103 has an opening so that a tube 105 extends from the center of the cover 103.

With continued reference to FIG. 2, the digester part of the chamber 101 includes a PEEK (polyetherketone) high temperature tee 107, a PEEK reaction coil 109, a second reaction call quartz made generally from quartz (hereinafter "quartz reaction coil" 111) and a heating pad/element 113. The Peek high temperature tee 107 has a first opening 107$a$ that receives a flow from an HLPC system, and a second opening 107$b$ that typically receives concentrated nitric acid ($HNO_3$,) so as to begin to mix with the flow of HPLC. Fluids entering the tee at 107$a$, 107$b$ exit the tee at 107$c$ and enter into the PEEK reaction coil 109.

However, it should be noted that while it is preferred that the sample-in-solvent and acid first begin to premix when exiting a common output of the tee 107, it is well within the spirit of the invention and the scope of the appended claims that either the sample-in-solvent or the acid could pass into the coil 109 consecutively.

Also, a person of ordinary skill in the art understands that it is within the spirit of the invention and the scope of the appended claims that there can be substitutes for the tee shown and described, for example, a collector vessel/premixing device that could provide as an output a combination of the sample-in-solvent and acid. While nitric acid is preferred, there could be a different acid other than nitric used in operation depending upon the material to be digested. The function is to perform the partial digestion, and there may be instances where different degrees of digestion are desired by either varying the type or possibly the concentration of acid used.

The PEEK reaction coil 109 is connected to the output of the tee 107$c$ so that the fluids exiting the tee 107 will begin to mix and start the acid digestion process. Additionally, as shown in FIG. 2, the PEEK reaction coil 109 is arranged outside of the chamber housing 101 and the fluids passing therein are exposed to room temperature during the beginning of the acid digestion process.

The Peek reaction coil 109 is connected to the quartz reaction coil 111. The reaction coil is preheated, typically on order of 250-300° C. There is a heating pad 113 arranged at the bottom of the chamber housing 101, which aids to assist in keeping the fluids passing through the quartz reaction coil 111 at the preheated temperature.

The sample is partially digested at this point and transferred to a vapor phase.

Figure 3:
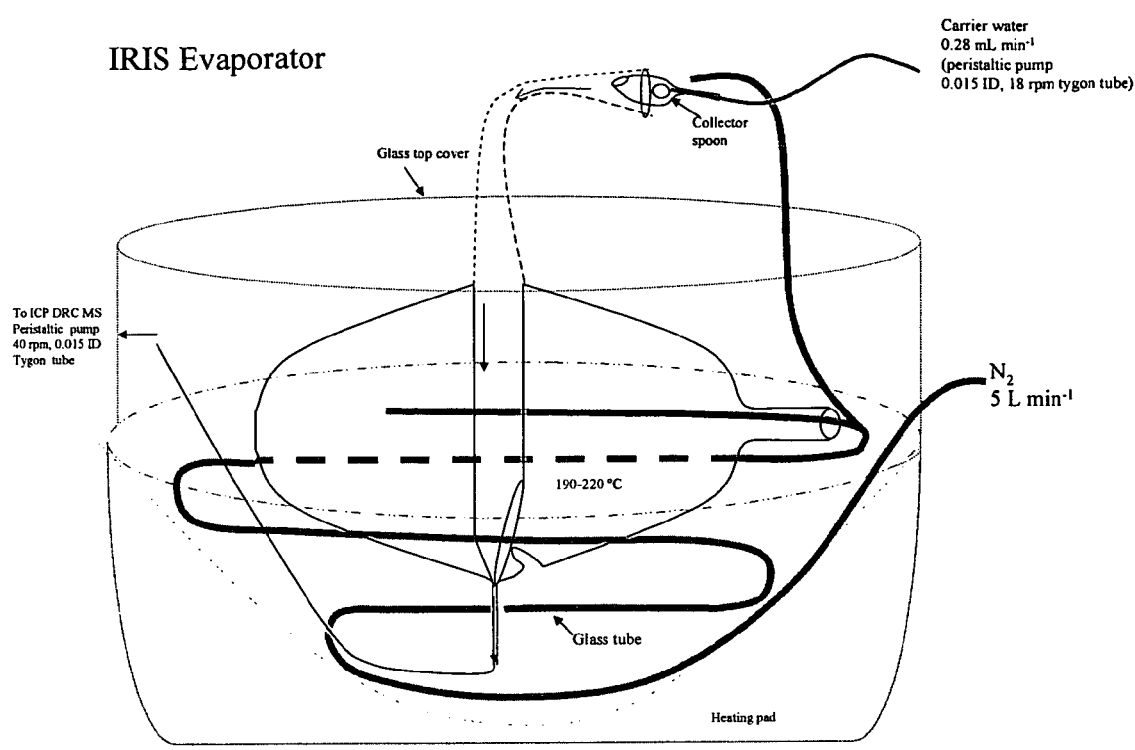
FIG. 3 is a schematic of the IRIS Evaporator of FIG. 2 without the digester portion.

FIG. 3 shows only the Evaporator portion, with the digester portion removed for clarity purposes. As there can be temperatures ranging as high as 300° C. during operation of the IRIS-DE interface device, the entire housing should be able to withstand such a high degree of heat. As discussed previously, the cover 103 has an opening in the vicinity of its center, and the opening is sized so as to receive an open tube 105 which allows the flow to coat the surface and increases the evaporative contact area with gas, said typically comprising a flow of preheated nitrogen gas.

For purposes of illustration and not for limitation, the nitric acid may typically have 1 ppb Se in 100% $HNO_3$, 0.28 mL/min using a peristaltic pump (not shown) 0.015 ID, 18 rpm tygon tube).

A collector spoon 115 is arranged within the open tube 105 (as shown by the arrows), via the throat of the open tube 105, and down into a lower portion close to the digester. The arrangement of the collector spoon 115 in the open tube 105 assists in the receipt/collection of sample vapor. Typically, some carrier water is placed on the collector spoon to enhance the vapor collection process. In addition, a glass tube 117 is used to supply pre-heated Nitrogen gas before it enters the evaporator chamber through an axial opening 119.

Figure 4:
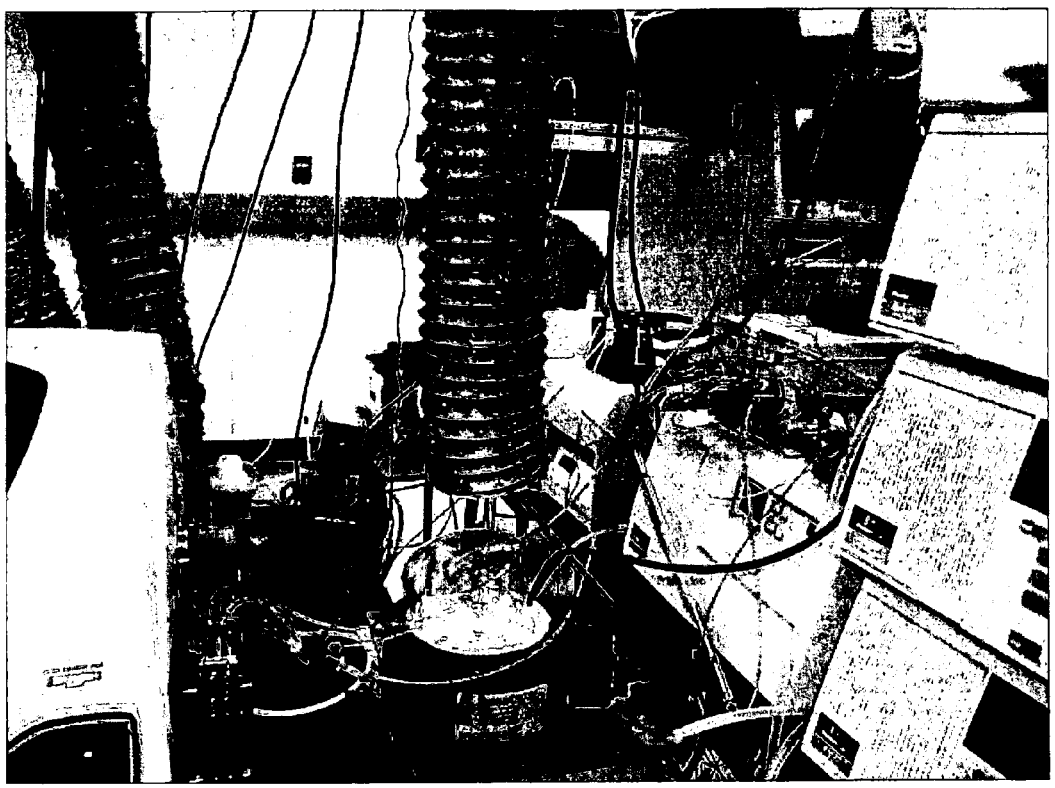
FIG. 4 is a photograph of the IRIS-DE interface under test conditions.

FIG. 4 is an actual photo of the IRIS-DE interface in use. There is a large venting duct above the apparatus.

FIGS. 5A and 5B are photographs of an actual collector spoon 115 used to collect a vapor sample according to the present invention.

FIG. 6 shows photographs of the alignment between the quartz coil, collector spoon 115, the nitrogen gas flow line 119, and the top entrance of the evaporator.

In operation, with reference to FIGS. 2-4, it should be noted that the IRIS-DE is coupled to the HPLC using reversed-phased (RP) chromatography processes HPLC effluent by digesting protein analytes with nitric acid, evaporates the undesirable high concentration excess of nitric acid and organic solvent on-line, and sends the sample to the ICP-MS, also coupled to the IRIS-DE at am output, in a highly aqueous stream. Through this process, a continuous flow received from reversed phase liquid chromatography systems with gradient elution can be easily handled by existing ICP-MS instruments.

More particularly, a flow of preheated nitrogen ($N_2$) in the line 119 and the preheated quartz chamber is used to evaporate the remaining nitric acid and most of the organic solvent from the sample mix. The sample travels through the open tube 105 (that goes into the chamber at the top).

The design of the IRIS-DE is such that the flow coats the surface and increases the evaporative contact area with the gas, so that molecules with lower boiling points evaporate first and are removed from the flow by the nitrogen gas; the organic solvent evaporates faster than the water. The nitrogen flows create a cyclonic gas flow into the chamber that, together with the glass cover, helps to maintain the chamber temperature. Also, the nitrogen gas acts as a carrier that sweeps vapor molecules from the flow, and sends them out the chamber through the top and axial openings.

When the flow reaches the chamber bottom, the digested sample is dissolved mainly in water. Then a peristaltic pump (not shown) is used to continuously pull flow from the evaporator chamber and send it into the ICP-MS.

The IRIS Evaporator shown in FIG. 3 can also be used to concentrate a low amount of analyte, by introducing a sample flow with a peristaltic pump that would replace the HPLC flow.

Figure 7:
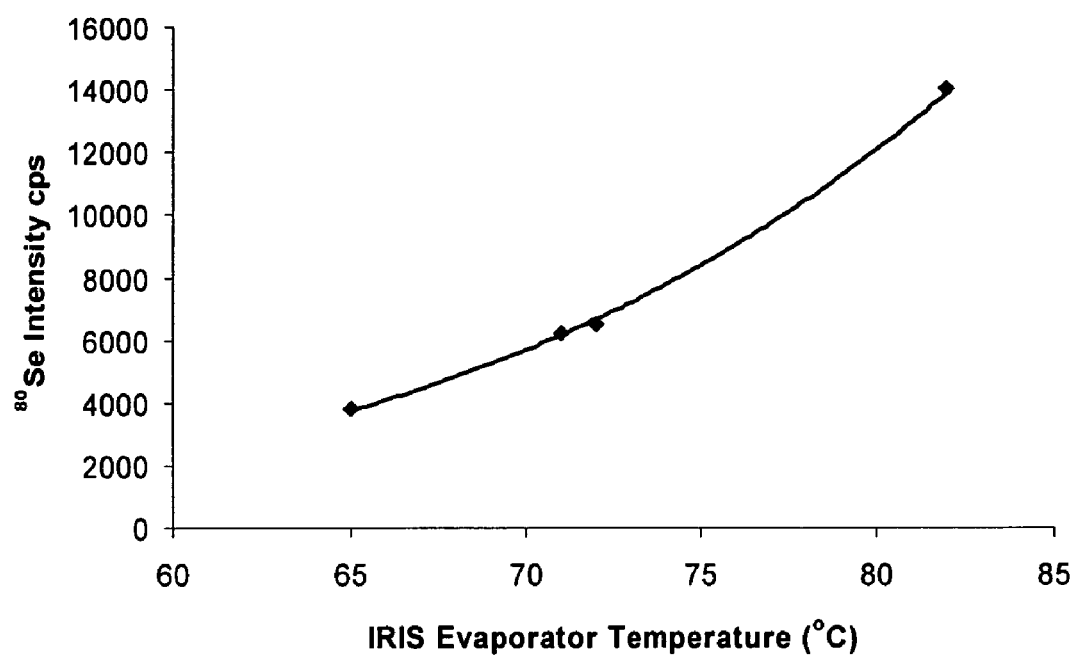
FIG. 7 is a graph of the intensity of the selenium versus the evaporator temperature.

FIG. 7 shows a graph of Iris Evaporator temperature versus the Se intensity. The IRIS evaporator capability was tested at temperatures less than 100° C. for 100% acetonitrile HPLC effluent. The HPLC instrument without a column was coupled to the ICP-DRC-ICP_MS instrument using the Iris evaporator shown in FIG. 3. The acetonitrile effluent flow rate was 0.25 ml min$^{-1}$. Four independent of 10 uL of a standard solution of selenium at 1 mg kg$^{-1}$ (prepared from NIST SRM 3149) were made at four different temperatures of the evaporator chamber, and the Se response was measured.

The IRIS-DE interface can be commercially implemented as an HPLC-ICP-MS interface system by construction in an enclosure fitted with a vacuum exhaust flow, and accurate control of variables. The variables for this device can include: the temperature of the digester and the evaporator, the nitrogen gas flow, the carrier water flow, the position of the collector spoon, the peristaltic pump removal and the physical dimensions.

Another advantage of the present invention is that the next run is unaffected by the previous run, resulting in a measurement system that is more robust than known heretofore. The reason is because virtually all of the organic solvent is eliminated online in a run of the IRIS-DE, so conditions such as nitrogen flow, temperature, and carrier water, can be optimized for each application. The dimensions can be modified to suit different flow rates. In addition, the system is able partially to digest the analyte before the solvent evaporation process.

While the invention has been described with reference to a specific example, a person of skill will certainly be able to achieve many other equivalent forms, all of which will come within the field and scope of the invention. For example, the invention is not limited to HPLC-ICP-MS applications, as it can be used as a faster on-line sample preparation device for ICP systems and also for flame atomic absorption spectrophotometry (FAAS).

We claim:

1. A digester-evaporator for partially digesting a sample mixed in a solvent with an acid and for evaporating the solvent and the acid after partial digestion, said digester-evaporator includes:
   a digester portion comprising:
   a reaction coil having an input and an output, said reaction coil adapted for receiving at its input a flow of a sample in a solvent and an acid suitable for partial digestion of the sample so as to begin mixing and partial digestion in the reaction coil;
   a heating element arranged along a portion of the reaction coil;
   at least a portion of the reaction coil proximate to its output being preheated by the heating element to a degree sufficient to convert a partially digested sample into vapor;
   a collector spoon with carrier water for collecting sample vapor; and an evaporator portion comprising:
   an evaporation chamber including a cover with a first opening having a substantially vertically-oriented tube extending from the cover, said evaporation chamber includes an axial opening longitudinally arranged therein, and said evaporation chamber adapted to contain fluid at a bottom portion;
   said collector spoon arranged in the top of the substantially vertically-oriented tube after a vapor sample has been collected from the digester portion;
   a gas supply tube for supplying a preheated gas provided in a top of the substantially vertically-oriented tube and in the axial opening of the evaporation chamber so as to create a cyclonic gas flow into the chamber and carry the sample to a container area in a bottom portion of the chamber;
   wherein an output of said evaporation chamber is in fluid communication with an output device.

2. The digester-evaporator according to claim 1, wherein said digester portion is coupled to a flow from a High Performance Liquid Chromatography (HPLC) device.

3. The digester-evaporator according to claim 2, wherein the HPLC device is reverse-phased.

4. The digester-evaporator according to claim 2, wherein the output device in fluid communication with the output of the evaporation chamber comprises an inductively coupled plasma-mass spectrometry (ICP-MS) device, the acid suitable for digestion of the sample comprises nitric acid, the solvent comprises an organic solvent, and the fluid contained in the container area of the chamber comprises water.

5. The digester-evaporator according to claim 1, wherein said digester portion includes:
   a tee connector being in fluid, communication with the input of said reaction coil in the digester portion, said tee having an output and two inputs, said tee being adapted to receive at a first input a sample in a solvent and output from a high performance liquid chromatography (HPLC) system, and for receiving at a second input of said tee an acid used in a digestion process of said sample in the solvent, wherein the sample in the solvent and the acid both exit the tee connector at its output.

6. The digester-evaporator according to claim 4, wherein said digester portion includes:
   a tee connector being in fluid communication with the input of said reaction coil in the digester portion, said tee having an output and two inputs, said tee being adapted to receive at a first input a sample in a solvent or output from a high performance liquid chromatography (HPLC) system, and for receiving at a second input of said tee an acid used in a digestion process of said sample in the solvent, wherein the sample in the solvent and the acid both exit the tee connector at its output.

7. The digester-evaporator according to claim 6, wherein the reaction coil comprises a (polyetherketone) PEEK reaction coil section connected to the output of the tee connector, the PEEK reaction coil section coupled to a quartz reaction coil section that includes said heating element.

8. The digester-evaporator according to claim 7, wherein the gas supply tube carries nitrogen gas that has been pre-heated by the heating element associated with the quartz reaction coil.

9. The digester-evaporator according to claim 7, further comprising a first peristaltic pump in communication with the bottom portion of the evaporation chamber.

10. The digester-evaporator according to claim 9, further comprising a second peristaltic pump for pumping acid into the tee connector.

11. The digester-evaporator according to claim 9, wherein the sample in a solvent comprises selenium-containing proteins.

* * * * *